(12) United States Patent
Minami et al.

(10) Patent No.: US 9,854,983 B2
(45) Date of Patent: Jan. 2, 2018

(54) ELECTRONIC APPARATUS AND OPERATION MANAGEMENT METHOD UTILIZING TEMPERATURE INFORMATION TO SUPPRESS TEMPERATURE EFFECTS CAUSED BY APPARATUS IN CONTACT WITH SKIN

(71) Applicant: CASIO COMPUTER CO., LTD., Tokyo (JP)

(72) Inventors: Tsuyoshi Minami, Musashimurayama (JP); Hiroshi Katsuda, Kodaira (JP)

(73) Assignee: CASIO COMPUTER CO., LTD. (JP)

( * ) Notice: Subject to any disclaimer, the term of this patent is extended or adjusted under 35 U.S.C. 154(b) by 0 days.

(21) Appl. No.: 15/076,306

(22) Filed: Mar. 21, 2016

(65) Prior Publication Data

US 2016/0374572 A1 Dec. 29, 2016

(30) Foreign Application Priority Data

Jun. 24, 2015 (JP) ................................. 2015-126739

(51) Int. Cl.
*A61B 5/01* (2006.01)
*A61B 5/024* (2006.01)
*A61B 5/107* (2006.01)
*A61B 5/00* (2006.01)

(52) U.S. Cl.
CPC ............ *A61B 5/02416* (2013.01); *A61B 5/01* (2013.01); *A61B 5/1075* (2013.01); *A61B 5/681* (2013.01); *A61B 5/684* (2013.01); *A61B 5/02438* (2013.01); *A61B 5/4809* (2013.01); *A61B 2560/0209* (2013.01)

(58) Field of Classification Search
None
See application file for complete search history.

(56) References Cited

U.S. PATENT DOCUMENTS

| 6,278,258 | B1 * | 8/2001 | Echarri | A61N 1/3708 |
| | | | | 320/130 |
| 6,542,846 | B1 * | 4/2003 | Miller | A61B 8/546 |
| | | | | 340/584 |
| 6,661,655 | B2 * | 12/2003 | Yin | G06F 1/181 |
| | | | | 165/127 |

(Continued)

FOREIGN PATENT DOCUMENTS

| JP | 2006-101505 A | 4/2006 |
| JP | 5497196 B2 | 5/2014 |

*Primary Examiner* — Kennedy Schaetzle
(74) *Attorney, Agent, or Firm* — Fitch Even Tabin & Flannery LLP (57) ABSTRACT

The effect of prolonged skin contact with an electronic apparatus is appropriately suppressed. An electronic apparatus 1 includes a temperature acquisition unit 54, a temperature integration unit 55, and a temperature management unit 56. The temperature acquisition unit 54 acquires the temperature of the apparatus. The temperature integration unit 55 acquires information (limit time) about the effect on the skin which changes depending on the temperature. The temperature management unit 56 executes a preset process, based on the temperature of the apparatus acquired by the temperature acquisition unit 54 and the information about the effect on the skin acquired by the temperature integration unit 55.

16 Claims, 4 Drawing Sheets

(56) References Cited

U.S. PATENT DOCUMENTS

| | | | | |
|---|---|---|---|---|
| 6,738,652 | B2* | 5/2004 | Mattu | A61B 5/0059 |
| | | | | 600/310 |
| 9,232,135 | B2* | 1/2016 | Kim | H04N 5/23241 |
| 2004/0050566 | A1* | 3/2004 | Totsu | B25B 21/00 |
| | | | | 173/2 |
| 2007/0239233 | A1* | 10/2007 | Klein | A61N 5/0616 |
| | | | | 607/88 |
| 2013/0253487 | A1* | 9/2013 | Liu | A61B 18/203 |
| | | | | 606/9 |
| 2013/0282085 | A1* | 10/2013 | Lischinsky | A61B 18/14 |
| | | | | 607/102 |

* cited by examiner

ELECTRONIC APPARATUS AND OPERATION MANAGEMENT METHOD UTILIZING TEMPERATURE INFORMATION TO SUPPRESS TEMPERATURE EFFECTS CAUSED BY APPARATUS IN CONTACT WITH SKIN

CROSS-REFERENCE TO RELATED APPLICATIONS

This application is based upon and claims the benefit of priority under 35 USC 119 of Japanese Patent Application No. 2015-126739 filed on Jun. 24, 2015, the entire disclosure of which, including the description, claims, drawings, and abstract, is incorporated herein by reference in its entirety.

BACKGROUND OF THE INVENTION

1. Field of the Invention

The present invention relates to an electronic apparatus, an operation management method, and a computer-readable medium.

2. Description of the Related Art

Wearable wrist terminals called smartwatches are becoming increasingly common in recent years as described in, for example, Japanese Patent Application Laid-Open No. 2006-101505. For instance, a user wears a smartwatch on his or her wrist at all times.

SUMMARY OF THE INVENTION

The present invention is an electronic apparatus including: a temperature acquisition unit operable to acquire a temperature of the apparatus; and a computing device operable to function as units including: an information acquisition unit operable to acquire information about an effect on a skin, wherein the information about the effect on the skin changes depending on the temperature and is based on a limit time associated with the temperature; and a processing unit operable to execute a preset process, based on the information about the effect on the skin acquired by the information acquisition unit for the temperature of the apparatus.

The present invention is an operation management method including: acquiring a temperature of the apparatus; acquiring information about an effect on a skin, wherein the information about the effect on the skin changes depending on the temperature and is based on a limit time associated with the temperature; and executing a preset process, based on the acquired information about the effect on the skin for the acquired temperature of the apparatus.

The present invention is a computer-readable medium in which a program is stored, the program causing a computer for controlling an electronic apparatus including a temperature acquisition unit operable to acquire a temperature of the apparatus, to realize: an information acquisition function of acquiring information about an effect on a skin, wherein the information about the effect on the skin changes depending on the temperature and is based on a limit time associated with the temperature; and a processing function of executing a preset process, based on the information about the effect on the skin acquired by the information acquisition function for the temperature of the apparatus acquired by the temperature acquisition unit.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION

Embodiments of the present invention will be explained with reference to the drawings.

Figure 1:
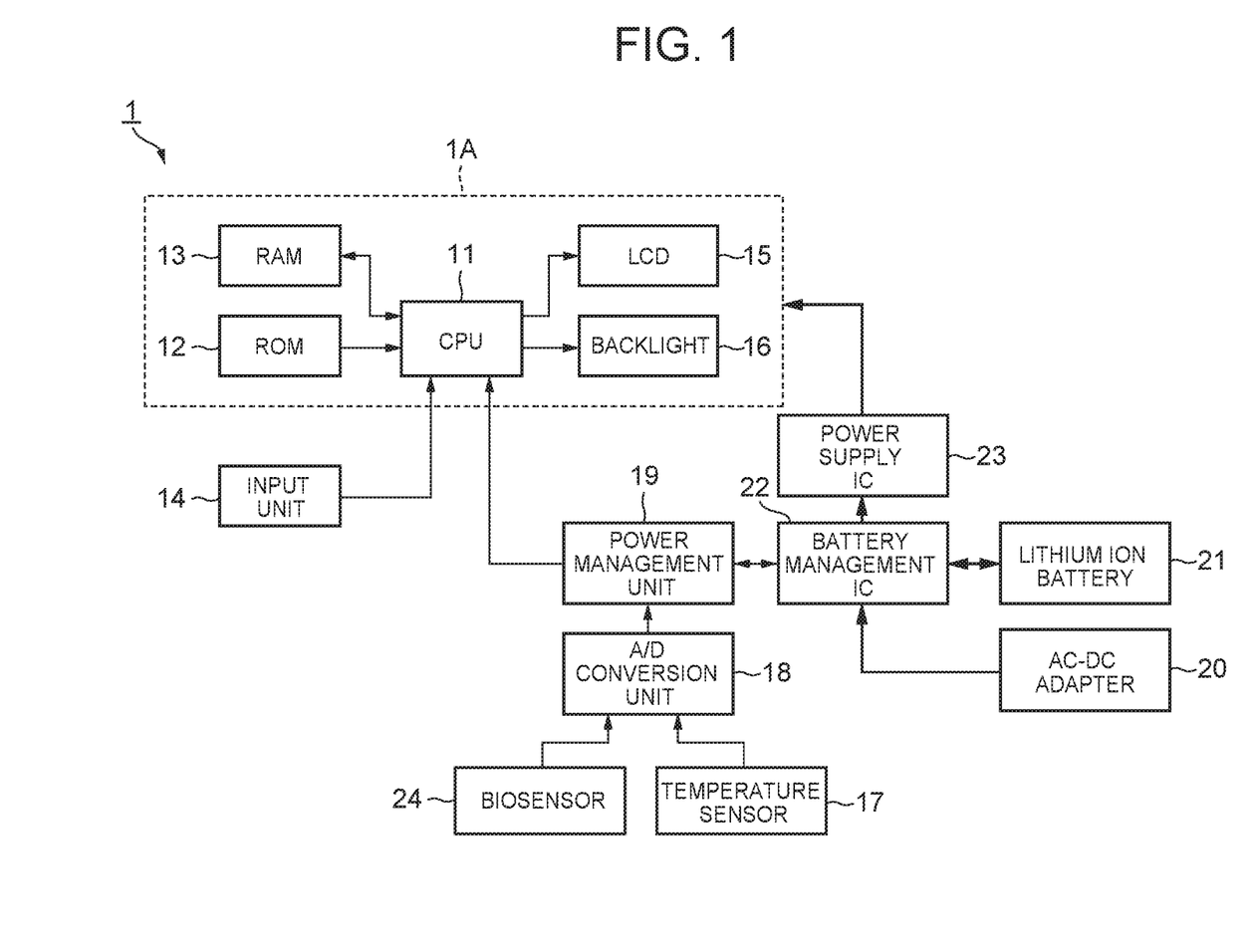
FIG. 1 is a block diagram illustrating the hardware structure of an electronic apparatus according to an embodiment of the present invention.

FIG. 1 is a block diagram illustrating the hardware structure of an electronic apparatus 1 according to an embodiment of the present invention.

The electronic apparatus 1 is, for example, a wrist terminal such as a smartwatch.

[Hardware Structure]

The electronic apparatus 1 includes a central processing unit (CPU) 11, a read only memory (ROM) 12, a random access memory (RAM) 13, an input unit 14, a liquid crystal display (LCD) 15, a backlight 16, a temperature sensor 17, an analog to digital (A/D) conversion unit 18, a power management unit 19, an AC-DC adapter 20, a lithium ion battery 21, a battery management IC 22, a power supply IC 23, and a biosensor 24. In the electronic apparatus 1, the CPU 11, the ROM 12, the RAM 13, the LCD 15, and the backlight 16 constitute an application processing unit 1A.

The CPU 11 executes various processes such as the below-mentioned power management process, according to programs stored in the ROM 12.

The ROM 12 stores various programs executed by the CPU 11 and various data used for the control of the electronic apparatus 1.

The RAM 13 stores data necessary for the execution of various processes by the CPU 11 and the like, as needed.

The input unit 14 includes various buttons, capacitance or resistive position input sensors layered in the display area of the LCD 15, etc., and receives input of various information according to user commands.

The LCD 15 outputs images according to instructions by the CPU 11. For example, the LCD 15 displays various images and user interface screens. In this embodiment, the position input sensors of the input unit 14 are overlaid on the LCD 15, constituting a touch panel.

The backlight 16 includes a light emitting diode (LED) and the like installed on the back of the LCD 15, and illuminates the LCD 15 from the back during display on the LCD 15. The LCD 15 and the backlight 16 may be replaced with a display panel (e.g. an organic EL panel) that emits light itself.

The temperature sensor 17 is installed on the back (the surface that comes into contact with the user) of the electronic apparatus 1 or the electronic apparatus 1 side of the back cover provided on the back of the electronic apparatus 1, and detects the temperature of the part of the electronic apparatus 1 in contact with the user.

The A/D conversion unit 18 converts an analog detection signal (voltage) indicating the temperature detected by the temperature sensor 17 into a digital signal (temperature), and outputs the digital signal to the power management unit 19. The A/D conversion unit 18 also converts an analog detection signal (voltage) indicating bio-information detected by the biosensor 24 into a digital signal (bio-information), and outputs the digital signal to the power management unit 19.

The power management unit 19 includes a microcomputer including a processor, memory, etc., and manages the power supply to the electronic apparatus 1. In detail, by executing the below-mentioned power management process, the power management unit 19 integrates the effect of the temperature on the user's skin based on the detection signals of the temperature sensor 17 and biosensor 24, and determines the integrated effect to manage (e.g. stop or resume) the power supply to the electronic apparatus 1.

The AC-DC adapter 20 converts an alternating current (AC) voltage output from a commercial power supply into a direct current (DC) voltage.

The lithium ion battery 21 is charged by the battery management IC 22, and also supplies the stored power to the battery management IC 22.

The battery management IC 22 charges the lithium ion battery 21 with the power supplied from the AC-DC adapter 20. The battery management IC 22 also supplies the power stored in the lithium ion battery 21 to the power supply IC 23.

The power supply IC 23 supplies power to the electronic apparatus 1 or stops the power supply, according to an instruction by the power management unit 19. Here, the power supply IC 23 converts the voltage supplied from the battery management IC 22 into a voltage specified for each part (e.g. the CPU 11, the LCD 15, or the like) as a power supply destination in the electronic apparatus 1, and supplies the power.

The biosensor 24 is installed on the back (the surface that comes into contact with the user) of the electronic apparatus 1, and detects the bio-information of the user by, for example, irradiating the user's skin with light and measuring the reflected light. In this embodiment, the biosensor 24 detects the user's pulse and whether or not the electronic apparatus 1 is in contact with the user's skin.

[Functional Structure]

Figure 2:
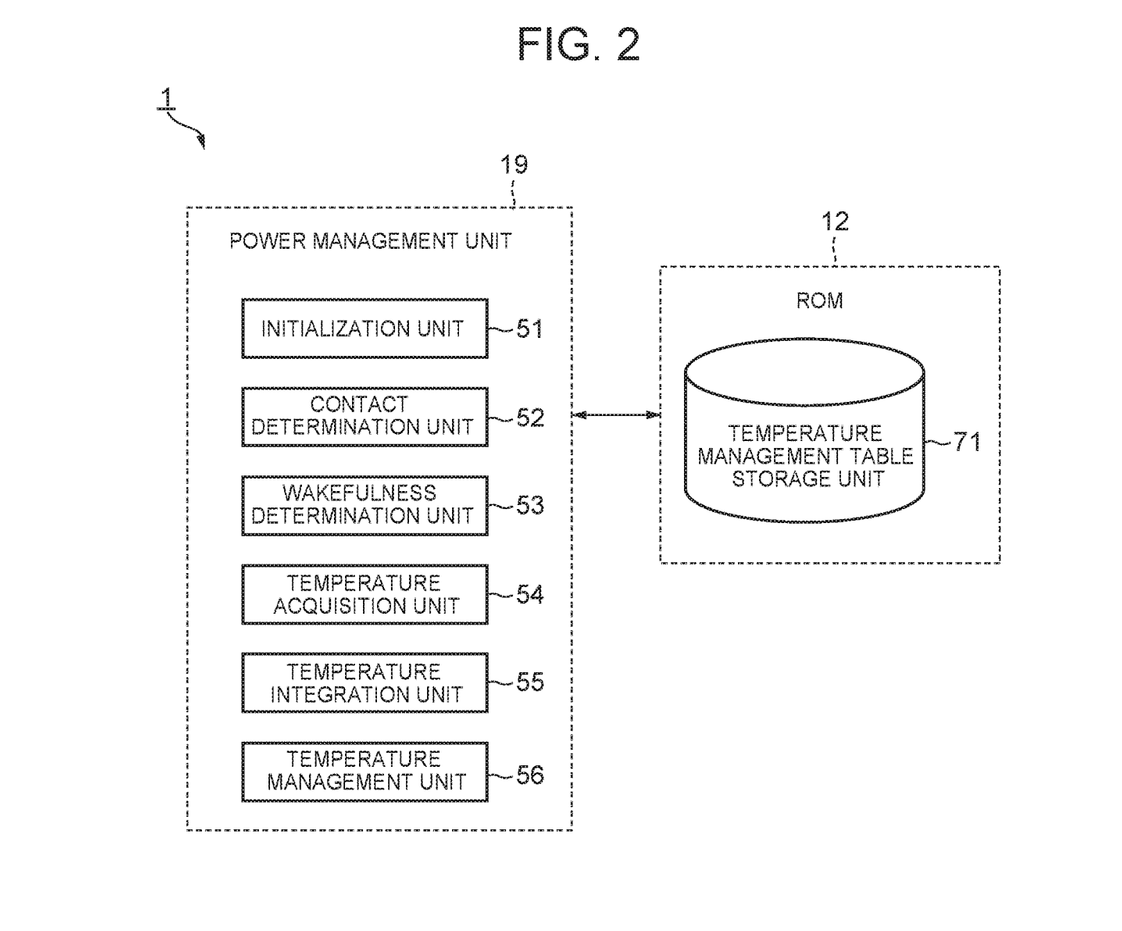
FIG. 2 is a functional block diagram illustrating the functional structure for executing a power management process in the functional structure of the electronic apparatus 1 in FIG. 1.

FIG. 2 is a functional block diagram illustrating the functional structure for executing the power management process in the functional structure of the electronic apparatus 1.

The power management process is a series of processes for managing the power supply to the electronic apparatus 1 according to conditions that take into consideration the past effect of the temperature of the electronic apparatus 1 on the skin, based on the temperature detected by the temperature sensor 17.

In the case of executing the power management process, the power management unit 19 functions as an initialization unit 51, a contact determination unit 52, a wakefulness determination unit 53, a temperature acquisition unit 54, a temperature integration unit 55, and a temperature management unit 56, as illustrated in FIG. 2.

Moreover, a temperature management table storage unit 71 is set in an area in the ROM 12.

The temperature management table storage unit 71 stores data of a temperature management table indicating, in tabular form, the relationship between the temperature of the electronic apparatus 1 and the time taken for the contact with the electronic apparatus 1 of the temperature to accumulate to affect the skin (e.g. a low temperature burn). In the temperature management table, each specific temperature and the time taken to affect the skin are associated with each other. In the case where the time taken for the temperature of the electronic apparatus 1 to affect the skin can be represented by a formula, however, the formula may be stored instead of the temperature management table. In other words, the time taken to affect the skin may be directly calculated from the measured temperature, instead of using the table.

The initialization unit 51 initializes (resets) the integration value (the below-mentioned integration value X) of the effect of the temperature on the user's skin, when the electronic apparatus 1 is activated.

The contact determination unit 52 determines whether or not the electronic apparatus 1 is in contact with the user's skin, based on the detection signal of the biosensor 24.

The wakefulness determination unit 53 acquires the user's pulse based on the detection signal of the biosensor 24, and determines the wakefulness of the user (whether the user is asleep or awake). In the case where the electronic apparatus 1 includes other sensors, such as an accelerometer and a gyroscope, which can be used to determine the wakefulness of the user, the wakefulness determination unit 53 can determine the wakefulness of the user based on the detection signals of these sensors in addition to the detection signal of the biosensor 24.

The temperature acquisition unit 54 acquires the temperature detected by the temperature sensor 17, via the A/D conversion unit 18.

The temperature integration unit 55 calculates a temperature coefficient based on the temperature acquired by the temperature acquisition unit 54, and acquires the integration value X of the temperature coefficient from when the temperature detection starts.

In detail, the temperature integration unit 55 sets the following limit times on the assumption that, for example, prolonged contact with the electronic apparatus 1 affects the skin in the case where the temperature of the electronic apparatus 1 is not less than 42 degrees C. Note that these values are merely illustrative, and experimental values according to the specifications of the electronic apparatus 1 may be employed in actual use.

42 degrees C.: 240 minutes
43 degrees C.: 145 minutes
44 degrees C.: 90 minutes
45 degrees C.: 50 minutes Suppose the skin is affected in the case where the integration value X of the temperature coefficient exceeds 100 as a threshold for stopping the power supply. Then, the temperature coefficient is as follows.

42 degrees C.: 100/240 (minutes)≈0.42
43 degrees C.: 100/145 (minutes)≈0.7
44 degrees C.: 100/90 (minutes)≈1.1
45 degrees C.: 100/50 (minutes)≈2

In the case where the temperature acquired by the temperature acquisition unit 54 is less than 42 degrees C., the temperature coefficient is as follows.

38 degrees C.: −100/20 (minutes)≈−5
40 degrees C.: −100/30 (minutes)≈−3.3
41 degrees C.: −100/40 (minutes)≈−2.5

The temperature coefficient indicates the effect on the skin per unit time. A negative temperature coefficient means that, in the case where the negative temperature continues, there is recovery from the effect of the temperature on the skin (recovery skin damage of low temperature burn) even when the skin is in contact with the electronic apparatus 1.

In the case where the temperature of the electronic apparatus 1 is less than 42 degrees C. immediately after the electronic apparatus 1 is powered on, for example, the temperature coefficient is set to not a negative value but 0. In this way, the integration value of the temperature coefficient is held at 0 until the temperature of the electronic apparatus 1 becomes 42 degrees C. or higher for the first time.

The temperature integration unit 55 calculates the temperature coefficient corresponding to the temperature per minute and adds the temperature coefficient to the past integration value X, thus sequentially calculating the integration value X.

The temperature management unit 56 determines whether or not the integration value X calculated by the temperature integration unit 55 exceeds a threshold of 100 for stopping the power supply. In the case of determining that the integration value X exceeds the threshold of 100 for stopping the power supply, the temperature management unit 56 warns the user (a warning about the possibility of affecting the skin) by display, sound, or the like, and stops the power supply to the application processing unit 1A after a predetermined time from the warning to the user or after input of a response by the user. In the case where the power management unit 19 is charging the lithium ion battery 21 from the AC-DC adapter 20, the temperature management unit 56 also instructs the power management unit 19 to stop the charging.

After determining that the integration value X exceeds the threshold of 100 for stopping the power supply, the temperature management unit 56 determines whether or not the integration value X calculated by the temperature integration unit 55 is below a threshold of 50 for resuming the power supply. In the case of determining that the integration value X is below the threshold of 50 for resuming the power supply, the temperature management unit 56 resumes the power supply to the application processing unit 1A after a predetermined time from a notification to the user (a notification that the possibility of affecting the skin has decreased) or after input of a response by the user. In the case where the temperature management unit 56 has instructed the power management unit 19 to stop charging the lithium ion battery 21 from the AC-DC adapter 20, the temperature management unit 56 also instructs the power management unit 19 to resume the charging.

Thus, even when the temperature of the electronic apparatus 1 has dropped below the temperature at or above which the skin is assumed to be affected, the temperature management unit 56 does not resume the power supply immediately, but resumes the power supply after the past effect of the temperature of the electronic apparatus 1 on the skin is reduced. The effect of prolonged skin contact with the electronic apparatus 1 can be appropriately suppressed in this way.

[Operation]

The following describes operation.

Figure 3:
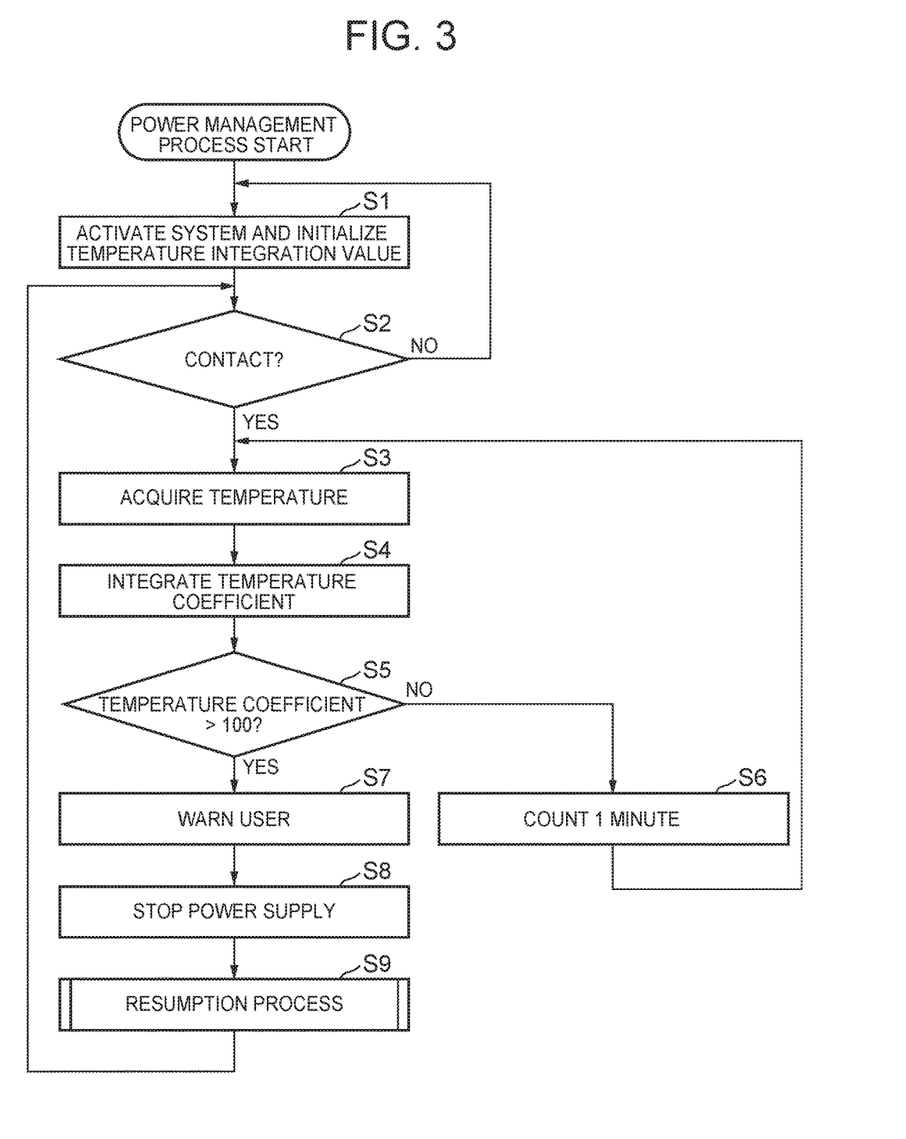
FIG. 3 is a flowchart illustrating the power management process executed by the electronic apparatus 1 in FIG. 1 having the functional structure in FIG. 2.

FIG. 3 is a flowchart illustrating the power management process executed by the electronic apparatus 1 in FIG. 1 having the functional structure in FIG. 2.

The power management process is started when the electronic apparatus 1 is powered on, and repeatedly executed until the electronic apparatus 1 is powered off.

In step S1, the initialization unit 51 executes the initialization process on the electronic apparatus 1. In detail, the initialization unit 51 activates each unit of the electronic apparatus 1, and resets (initializes) the integration value X of the temperature coefficient to 0.

In step S2, the contact determination unit 52 determines whether or not the electronic apparatus 1 is in contact with the user's skin, based on the detection signal of the biosensor 24.

In the case where the electronic apparatus 1 is not in contact with the user's skin, the determination in step S2 results in NO, and the process goes to step S1.

In the case where the electronic apparatus 1 is in contact with the user's skin, the determination in step S2 results in YES, and the process goes to step S3.

In step S3, the temperature acquisition unit 54 acquires the temperature detected by the temperature sensor 17, via the A/D conversion unit 18.

In step S4, the temperature integration unit 55 calculates the temperature coefficient based on the temperature acquired by the temperature acquisition unit 54, and acquires the integration value X of the temperature coefficient from when the temperature detection starts.

In step S5, the temperature management unit 56 determines whether or not the integration value X calculated by the temperature integration unit 55 exceeds the threshold of 100 for stopping the power supply.

In the case where the integration value X calculated by the temperature integration unit 55 does not exceed the threshold of 100 for stopping the power supply, the determination in step S5 results in NO, and the process goes to step S6.

In the case where the integration value X calculated by the temperature integration unit 55 exceeds the threshold of 100 for stopping the power supply, the determination in step S5 results in YES, and the process goes to step S7.

In step S6, the temperature management unit 56 counts 1 minute, and then the process goes to step S3.

In step S7, the temperature management unit 56 warns the user (a warning that the skin may be affected). For example, a warning that the temperature is too high may be given to the user by display on the LCD 15, sound output from a speaker (not illustrated), or both of them. In the case where the wakefulness determination unit 53 determines that the user is asleep, the temperature management unit 56 may omit the warning to the user in step S7.

In step S8, the temperature management unit 56 stops the power supply to the application processing unit 1A. Here, the temperature management unit 56 stops the power supply to the application processing unit 1A, after a predetermined time from the warning to the user in step S7 or after input of a response by the user. In the case where the power management unit 19 is charging the lithium ion battery 21 from the AC-DC adapter 20, the temperature management unit 56 also instructs the power management unit 19 to stop the charging.

Figure 4:
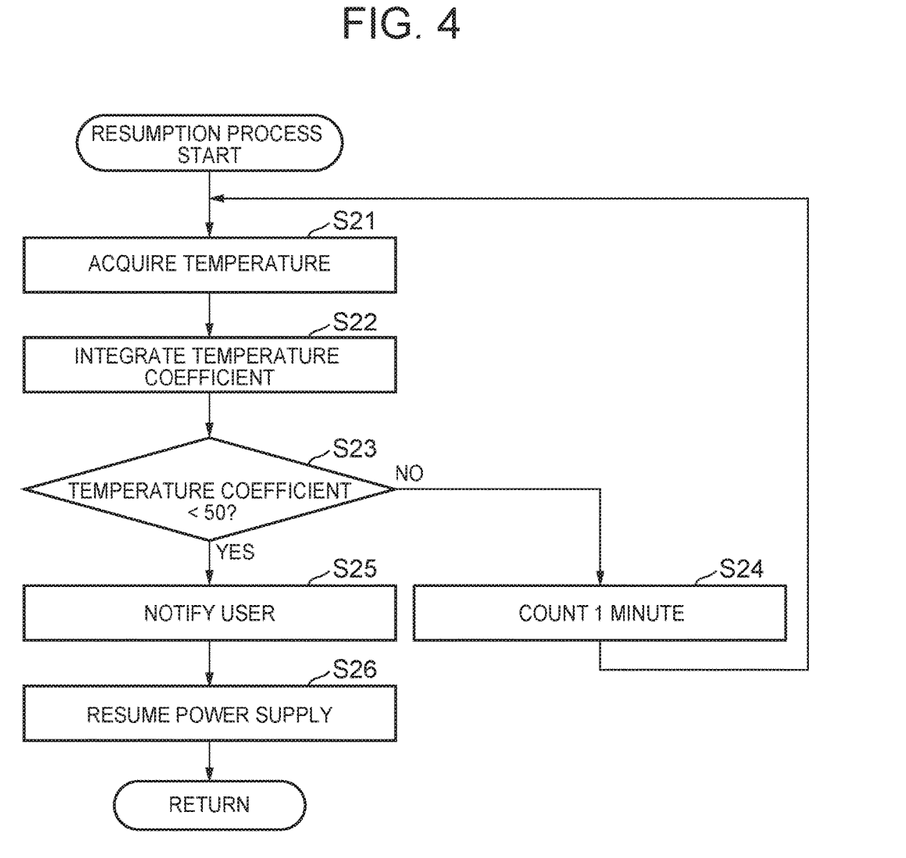
FIG. 4 is a flowchart illustrating a resumption process.

In step S9, the temperature management unit 56 executes a resumption process for resuming the power supply to the application processing unit 1A (see FIG. 4).

After step S9, the process goes to step S2.

The power management process described above is repeated until the electronic apparatus 1 is powered off.

According to such a process, while the electronic apparatus 1 is in contact with the user's skin, the effect on the user's skin is integrated as the temperature coefficient corresponding to the temperature and, in the case where the integration value exceeds the threshold, the user is warned of the effect on the skin and the power supply to the application processing unit 1A and the charging are stopped.

The effect of prolonged skin contact with the electronic apparatus 1 can be appropriately suppressed in consideration of the past effect of the temperature of the electronic apparatus 1 on the skin in this way.

The following describes the resumption process executed in step S9 in the temperature management process.

FIG. 4 is a flowchart illustrating the resumption process.

In step S21, the temperature acquisition unit 54 acquires the temperature detected by the temperature sensor 17, via the A/D conversion unit 18.

In step S22, the temperature integration unit 55 calculates the temperature coefficient based on the temperature acquired by the temperature acquisition unit 54, and acquires the integration value X of the temperature coefficient from when the temperature detection starts.

In step S23, the temperature management unit 56 determines whether or not the integration value X calculated by the temperature integration unit 55 is below the threshold of 50 for resuming the power supply.

In the case where the integration value X calculated by the temperature integration unit 55 is not below the threshold of 50 for resuming the power supply, the determination in step S23 results in NO, and the process goes to step S24.

In the case where the integration value X calculated by the temperature integration unit 55 is below the threshold of 50 for resuming the power supply, the determination in step S23 results in YES, and the process goes to step S25.

In step S24, the temperature management unit 56 counts 1 minute, and then the process goes to step S21.

In step S25, the temperature management unit 56 notifies the user (a notification that the possibility of affecting the skin has decreased). For example, a notification that the temperature has decreased may be given to the user by display on the LCD 15, sound output from a speaker (not illustrated), or both of them, as in step S7. In the case where the wakefulness determination unit 53 determines that the user is asleep, the temperature management unit 56 may omit the notification to the user in step S25.

In step S26, the temperature management unit 56 resumes the power supply to the application processing unit 1A. Here, the temperature management unit 56 resumes the power supply to the application processing unit 1A, after a predetermined time from the notification to the user in step S25 or after input of a response by the user. In the case where the temperature management unit 56 has instructed the power management unit 19 to stop charging the lithium ion battery 21 from the AC-DC adapter 20, the temperature management unit 56 also instructs the power management unit 19 to resume the charging.

After step S26, the process returns to the power management process.

According to such a process, even when the temperature of the electronic apparatus 1 has dropped below the temperature at or above which the skin is assumed to be affected, the temperature management unit 56 does not resume the power supply immediately, but resumes the power supply after the past effect of the temperature of the electronic apparatus 1 on the skin is reduced. The effect of prolonged skin contact with the electronic apparatus 1 can be appropriately suppressed in this way.

[Modification 1]

In the foregoing embodiment, the biosensor 24 may detect the skin type (skin thickness, etc.) of the user, and the threshold for stopping the power supply and the threshold for resuming the power supply may be changed depending on the detection result.

For example, in the case where the detected skin type is less susceptible to the temperature (i.e. the skin is thicker than a reference thickness), the temperature management unit 56 raises the threshold for stopping the power supply from 100 to 110, and lowers the threshold for resuming the power supply from 50 to 40. In the case where the detected skin type is more susceptible to the temperature (i.e. the skin is thinner than the reference thickness), the temperature management unit 56 lowers the threshold for stopping the power supply from 100 to 90, and raises the threshold for resuming the power supply from 50 to 60.

This enables such control that facilitates the power supply in the case where the user's skin is less susceptible to the temperature and facilitates stopping the power supply in the case where the user's skin is more susceptible to the temperature, depending on the skin type of the user.

[Modification 2]

The foregoing embodiment describes an example where the warning in step S7 in the temperature management process and the notification in step S25 in the resumption process are omitted in the case where the wakefulness determination unit 53 determines that the user is asleep.

Alternatively, the threshold for stopping the power supply and the threshold for resuming the power supply may be changed in the case where the wakefulness determination unit 53 determines that the user is asleep.

For example, in the case where the wakefulness determination unit 53 determines that the user is asleep, the threshold for stopping the power supply is lowered from 100 to 90, and the threshold for resuming the power supply is raised from 50 to 60.

This enables such control that facilitates stopping the power supply in the case where the user is asleep, with it being possible to prevent the user from being affected by the temperature without being aware of it during sleep.

In the case of determining that the user is asleep, the power supply to the LCD 15 and the backlight 16 or the application processing unit 1A may be stopped on the assumption that the user is not viewing the LCD 15.

The electronic apparatus 1 having the structure described above includes the temperature acquisition unit 54, the temperature integration unit 55, and the temperature management unit 56.

The temperature acquisition unit 54 acquires the temperature of the apparatus.

The temperature integration unit 55 acquires information (limit time) about the effect on the skin which changes depending on the temperature.

The temperature management unit 56 executes a preset process, based on the temperature of the apparatus acquired by the temperature acquisition unit 54 and the information about the effect on the skin acquired by the temperature integration unit 55.

Thus, while the electronic apparatus 1 is in contact with the user's skin, the information about the effect on the skin which changes depending on the temperature is acquired, and the preset process in the electronic apparatus 1 is executed according to the temperature of the apparatus and the information.

The effect of prolonged skin contact with the electronic apparatus 1 can be appropriately suppressed in this way.

The temperature integration unit 55 acquires an index (the integration value X of the temperature coefficient) of the effect of the temperature of the apparatus acquired by the temperature acquisition unit 54 on the user's skin up to the present, based on the temperature of the apparatus acquired by the temperature acquisition unit 54 and the information about the effect on the skin.

Thus, while the electronic apparatus 1 is in contact with the user's skin, the index of the effect on the user's skin is acquired, and the preset process in the electronic apparatus 1 is executed according to the index.

The effect of prolonged skin contact with the electronic apparatus 1 can be appropriately suppressed in consideration of the past effect of the temperature of the electronic apparatus 1 on the skin in this way.

The temperature integration unit 55 increases the index in the case where the temperature of the electronic apparatus 1 is not less than a threshold temperature set with regard to the effect of the temperature of the electronic apparatus 1 on the user's skin, and decreases the index in the case where the temperature of the electronic apparatus 1 is less than the threshold temperature.

Thus, the index can be changed depending on whether or not the temperature of the electronic apparatus 1 is not less than the threshold temperature, which enables appropriate control of the electronic apparatus 1.

The temperature integration unit 55 calculates a unit index (temperature coefficient) indicating the effect on the skin per unit time, based on the temperature of the electronic apparatus 1 acquired by the temperature acquisition unit 54 and a time set in association with the temperature.

The temperature integration unit 55 integrates the unit index per unit time, to acquire the index.

Thus, the index of the effect of the temperature of the electronic apparatus 1 on the user's skin up to the present can be acquired by appropriately reflecting the effect of the temperature per unit time.

The electronic apparatus 1 further includes the contact determination unit 52.

The contact determination unit 52 determines whether or not the apparatus is in contact with the user's skin.

The temperature integration unit 55 acquires the index up to the present from when the contact determination unit 52 determines that the apparatus is in contact with the user's skin.

Thus, the index of the effect of the temperature of the electronic apparatus 1 on the user's skin up to the present can be acquired by appropriately reflecting the effect during the time when the electronic apparatus 1 is actually in contact with the user's skin.

The temperature management unit 56 executes a process of suppressing the operation of the electronic apparatus 1 as the preset process, in the case where the index acquired by the temperature integration unit 55 exceeds a criterion for suppressing the operation.

Thus, the temperature of the electronic apparatus 1 can be decreased in the case where the index of the effect of the temperature of the electronic apparatus 1 on the user's skin up to the present exceeds the criterion for suppressing the operation.

The electronic apparatus 1 further includes the biosensor 24.

The biosensor 24 acquires the thickness of the user's skin.

The temperature management unit 56 raises the criterion for suppressing the operation in the case where the thickness of the user's skin acquired by the biosensor 24 is not less than a reference thickness, and lowers the criterion for suppressing the operation in the case where the thickness of the user's skin acquired by the biosensor 24 is less than the reference thickness.

This enables such control that facilitates the operation of the electronic apparatus 1 in the case where the user's skin is less susceptible to the temperature and facilitates suppressing the operation of the electronic apparatus 1 in the case where the user's skin is more susceptible to the temperature, depending on the skin type of the user.

The electronic apparatus 1 further includes the wakefulness determination unit 53.

The wakefulness determination unit 53 determines the wakefulness of the user.

The temperature management unit 56 lowers the criterion for suppressing the operation, in the case where the wakefulness determination unit 53 determines that the user is asleep.

This enables such control that facilitates suppressing the operation of the electronic apparatus 1 in the case where the user is asleep, with it being possible to prevent the user from being affected by the temperature without being aware of it during sleep.

The temperature management unit 56 releases the suppression of the operation of the electronic apparatus, in the case where the index acquired by the temperature integration unit 55 is below a criterion for releasing the suppression of the operation.

Thus, even when the temperature of the electronic apparatus 1 has dropped below the temperature at or above which the skin is assumed to be affected, the power supply is not resumed immediately, but resumed after the past effect of the temperature of the electronic apparatus 1 on the skin is reduced.

The effect of prolonged skin contact with the electronic apparatus 1 can be appropriately suppressed in this way.

The temperature management unit 56 notifies the execution of the preset process, when executing the preset process.

This enables the user to recognize that the situation requires the execution of the present process and that the preset process is to be executed.

The present invention is not limited to the foregoing embodiment, and includes changes and modifications as long as the object of the present invention is achieved.

Although the foregoing embodiment describes an example where the temperature management unit 56 stops the power supply to the application processing unit 1A in the electronic apparatus 1 in the case of determining that the integration value X calculated by the temperature integration unit 55 exceeds the threshold of 100 for stopping the power supply, this is not a limitation. The temperature management unit 56 may refer to the temperature acquired by the temperature acquisition unit 54 and, in the case of determining that a threshold for the information about the effect on the skin which changes depending on the temperature is exceeded, perform a predetermined process (e.g. stopping the power supply to the application processing unit 1A in the electronic apparatus 1).

Likewise, although the foregoing embodiment describes an example where the temperature management unit 56 resumes the power supply to the application processing unit 1A in the electronic apparatus 1 in the case of determining that the integration value X calculated by the temperature integration unit 55 is below the threshold of 50 for resuming the power supply, this is not a limitation. The temperature management unit 56 may refer to the temperature acquired by the temperature acquisition unit 54 and, in the case of determining that a threshold for the information about the effect on the skin which changes depending on the temperature is not exceeded, perform a predetermined process (e.g.

resuming the power supply to the application processing unit 1A in the electronic apparatus 1).

Although the foregoing embodiment describes an example where the temperature management unit 56 warns the user (a warning that the skin may be affected) and stops the power supply to the application processing unit 1A in the case where the integration value X calculated by the temperature integration unit 55 exceeds the threshold of 100 for stopping the power supply, the temperature management unit 56 may only warn the user without stopping the power supply to the application processing unit 1A. After the warning to the user, the user may select whether or not to stop the power supply to the application processing unit 1A.

Although the foregoing embodiment describes an example where the temperature management unit 56 stops the power supply to the application processing unit 1A or the charging of the lithium ion battery 21 in order to control the temperature of the electronic apparatus 1, this is not a limitation.

The temperature management unit 56 may decrease the operation clock in the application processing unit 1A or make the operation of the application processing unit 1A and the charging of the lithium ion battery 21 intermittent, as long as the temperature of the electronic apparatus 1 can be decreased.

Although the foregoing embodiment describes an example where the power management process is executed in the case where the contact determination unit 52 determines that the electronic apparatus 1 is in contact with the user's skin, this is not a limitation. The power management process may be suspended when the user removes the electronic apparatus 1 and, after the integration of the effect on the skin (recovery) during the suspension, resumed from when the user puts on the electronic apparatus 1 again.

Although the foregoing embodiment describes a wrist terminal as an example of the electronic apparatus 1 to which the present invention is applied, the present invention is not particularly limited to such.

For example, the present invention is applicable to electronic apparatuses used in contact with users in general. In detail, the present invention is applicable to a notebook personal computer, a television receiver, a video camera, a portable navigation device, a mobile phone, a smartphone, a portable game machine, any type of wearable terminal, etc.

The series of processes described above may be executed by hardware or by software.

In other words, the functional structure in FIG. 2 is merely illustrative, and does not particularly limit the present invention. As long as the electronic apparatus 1 has functions for executing the series of processes as a whole, which functional blocks are used to realize such functions is not particularly limited to the example in FIG. 2.

Furthermore, one functional block may be realized by hardware alone, by software alone, or by a combination of hardware and software.

In the case where the series of processes is executed by software, a program constituting the software is installed from a network or a recording medium into a computer or the like.

The computer may be a computer incorporated in dedicated hardware. The computer may be a computer capable of various functions when installed with various programs, such as a general-purpose personal computer.

A recording medium including such a program may be realized not only by a removable medium which is distributed separately from the apparatus to provide the program to the user, but also by, for example, a recording medium provided to the user in the state of being incorporated in the apparatus beforehand. The removable medium is, for example, a magnetic disk (such as a floppy disk), an optical disc, or a magneto-optical disc. Examples of the optical disc include a compact disc read-only memory (CD-ROM), a digital versatile disc (DVD), and a Blu-ray® disc. Examples of the magneto-optical disc include a mini disc (MD). The recording medium provided to the user in the state of being incorporated in the apparatus beforehand is, for example, the ROM 12 in FIG. 1 in which the program is stored.

In this specification, the steps included in the program stored in the recording medium may include not only processes executed in time series but also processes not executed in time series but executed in parallel or separately.

While some embodiments of the present invention have been described above, these embodiments are merely illustrative and do not limit the technical scope of the present invention. Various other embodiments of the present invention are possible, and changes such as omission and replacement may be made without departing from the scope of the present invention. These embodiments and modifications are included in the scope of the invention described in this specification as an example and also included in the scope of the invention described in the claims and its equivalent scope.

What is claimed is:

1. An electronic apparatus comprising:
   a temperature acquisition unit operable to acquire a temperature of the apparatus; and
   a computing device operable to function as units comprising:
   an information acquisition unit operable to acquire information about an effect on a skin, wherein the information about the effect on the skin changes depending on the temperature and is based on a limit time associated with the temperature; and
   a processing unit operable to execute a preset process, based on the information about the effect on the skin acquired by the information acquisition unit for the temperature of the apparatus,
   wherein the information acquisition unit is operable to acquire an index of the effect of the temperature of the apparatus on a user's skin up to present as the information about the effect on the skin.

2. The electronic apparatus according to claim 1, wherein the information acquisition unit is operable to increase the index in the case where the temperature of the apparatus is not less than a threshold temperature set with regard to the effect of the temperature of the apparatus on the user's skin, and decrease the index in the case where the temperature of the apparatus is less than the threshold temperature.

3. The electronic apparatus according to claim 1, further comprising
   a unit index calculation unit operable to calculate a unit index indicating the effect on the skin per unit time, based on the temperature of the apparatus and a time set in association with the temperature,
   wherein the information acquisition unit is operable to integrate the unit index per unit time, to acquire the index.

4. The electronic apparatus according to claim 1, further comprising
   a contact determination unit operable to determine whether or not the apparatus contacts the user's skin,
   wherein the information acquisition unit is operable to acquire the index up to the present from when the contact determination unit determines that the apparatus contacts the user's skin.

5. The electronic apparatus according to claim 1, wherein the processing unit is operable to execute a process of suppressing an operation of the electronic apparatus as the preset process, in the case where the index exceeds a criterion for suppressing the operation.

6. The electronic apparatus according to claim 5, further comprising
a thickness acquisition unit operable to acquire a thickness of the user's skin,
wherein the processing unit is operable to raise the criterion for suppressing the operation in the case where the thickness of the user's skin detected by the thickness acquisition unit is not less than a reference thickness, and lower the criterion for suppressing the operation in the case where the thickness of the user's skin detected by the thickness acquisition unit is less than the reference thickness.

7. The electronic apparatus according to claim 5, further comprising
a wakefulness determination unit operable to determine wakefulness of the user,
wherein the processing unit is operable to lower the criterion for the index, in the case where the wakefulness determination unit determines that the user is asleep.

8. The electronic apparatus according to claim 5,
wherein the processing unit is operable to release the suppression of the operation of the electronic apparatus, in the case where the index acquired by the information acquisition unit is below a criterion for releasing the suppression of the operation.

9. The electronic apparatus according to claim 1,
wherein the processing unit comprises
a notification unit operable to notify the execution of the preset process, when the processing unit executes the preset process.

10. An electronic apparatus comprising:
a temperature acquisition unit operable to acquire a temperature of the apparatus; and
a computing device operable to function as units comprising:
an information acquisition unit operable to acquire information about an effect on a user's skin, wherein the information about the effect on the skin changes depending on the temperature and is based on a limit time associated with the temperature; and
a processing unit operable to execute a preset process, based on the information about the effect on the skin acquired by the information acquisition unit for the temperature of the apparatus,
wherein the information acquisition unit is operable to acquire the information about the effect on the skin, based on a table indicating a relationship between the temperature of the apparatus and a time set in association with the temperature.

11. An electronic apparatus comprising:
a temperature acquisition unit operable to acquire a temperature of the apparatus; and
a computing device operable to function as units comprising:
an information acquisition unit operable to acquire information about an effect on a user's skin, wherein the information about the effect on the skin changes depending on the temperature and is based on a limit time associated with the temperature; and
a processing unit operable to execute a preset process, based on the information about the effect on the skin acquired by the information acquisition unit for the temperature of the apparatus,
wherein the information acquisition unit is operable to acquire the information about the effect on the skin, by calculating the information about the effect on the skin from the temperature of the apparatus.

12. An operation management method comprising:
acquiring a temperature of an apparatus;
acquiring information about an effect on a skin, wherein the information about the effect on the skin changes depending on the temperature and is based on a limit time associated with the temperature,
executing a preset process, based on the acquired information about the effect on the skin for the acquired temperature of the apparatus; and
acquiring an index of the effect of the acquired temperature of the apparatus on a user's skin up to present, based on the acquired temperature of the apparatus and the acquired information about the effect on the skin.

13. The operation management method according to claim 12, comprising
increasing the index in the case where the temperature of the apparatus is not less than a threshold temperature set with regard to the effect of the temperature of the apparatus on the user's skin, and decreasing the index in the case where the temperature of the apparatus is less than the threshold temperature.

14. The operation management method according to claim 12, comprising:
calculating a unit index indicating the effect on the skin per unit time, based on the acquired temperature of the apparatus and a time set in association with the temperature; and
integrating the calculated unit index per unit time, to acquire the index.

15. An operation management method comprising:
acquiring a temperature of an apparatus;
acquiring information about an effect on a user's skin, wherein the information about the effect on the skin changes depending on the temperature and is based on a limit time associated with the temperature; and
executing a preset process, based on the information about the effect on the skin acquired by the information acquisition unit for the temperature of the apparatus,
wherein the information about the effect on the skin is acquired based on a table indicating a relationship between the temperature of the apparatus and a time set in association with the temperature.

16. An operation management method comprising:
acquiring a temperature of an apparatus;
acquiring information about an effect on a user's skin, wherein the information about the effect on the skin changes depending on the temperature and is based on a limit time associated with the temperature; and
executing a preset process, based on the information about the effect on the skin acquired by the information acquisition unit for the temperature of the apparatus,
wherein the information about the effect on the skin is acquired by calculating the information about the effect on the skin from the temperature of the apparatus.

* * * * *